United States Patent
Ujihara et al.

(10) Patent No.: US 9,671,356 B2
(45) Date of Patent: Jun. 6, 2017

(54) METHOD AND DEVICE FOR MEASURING ENERGY OF ELECTRONS EXCITED BY SUNLIGHT

(71) Applicant: NATIONAL UNIVERSITY CORPORATION NAGOYA UNIVERSITY, Nagoya-shi, Aichi (JP)

(72) Inventors: Toru Ujihara, Nagoya (JP); Fumiaki Ichihashi, Nagoya (JP); Daiki Shimura, Nagoya (JP); Makoto Kuwahara, Nagoya (JP); Shunta Harada, Nagoya (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 0 days.

(21) Appl. No.: 14/655,970

(22) PCT Filed: Dec. 24, 2013

(86) PCT No.: PCT/JP2013/084497
§ 371 (c)(1),
(2) Date: Jun. 26, 2015

(87) PCT Pub. No.: WO2014/104022
PCT Pub. Date: Jul. 3, 2014

(65) Prior Publication Data
US 2016/0047760 A1    Feb. 18, 2016

(30) Foreign Application Priority Data

Dec. 27, 2012 (JP) ................. 2012-285579

(51) Int. Cl.
*G01N 23/223*  (2006.01)
*G01N 23/227*  (2006.01)
(Continued)

(52) U.S. Cl.
CPC .......... *G01N 23/2273* (2013.01); *H01J 49/48* (2013.01); *H01L 22/12* (2013.01); *H01L 31/035236* (2013.01); *H02S 50/15* (2014.12)

(58) Field of Classification Search
CPC ...... G01N 23/2273; H02S 50/15; H01J 49/48; H01L 22/12
See application file for complete search history.

(56) References Cited

U.S. PATENT DOCUMENTS 5,180,951 A * 1/1993 Dworsky ................ H01J 1/304
                                                                 313/311
6,104,029 A   8/2000 Coxon et al.
(Continued)

FOREIGN PATENT DOCUMENTS

JP   H02-144844 A   6/1990
JP   H10-188781 A   7/1998
JP   2008-078369 A  4/2008

OTHER PUBLICATIONS

Photoemission study of the negative electron affinity surfaces of O/Cs/Si(001)2×1 and O/K/Si(001)2×1 T. Abukawa, Y. Enta, T. Kashiwakura, S. Suzuki, S. Kono, and T. Sakamoto Citation: Journal of Vacuum Science & Technology A 8, 3205 (1990); doi: 10.1116/1.576564.*

(Continued)

*Primary Examiner* — Nicole Ippolito
*Assistant Examiner* — Sean Luck
(74) *Attorney, Agent, or Firm* — Oliff PLC

(57) ABSTRACT

A technique of measuring energy of electrons excited by exposing a semiconductor material to solar ray is proposed. A surface layer having a negative electron affinity is formed on the surface of a semiconductor material. The semiconductor material is placed in a vacuum environment and exposed to solar ray. Photoelectrons emitted from the surface layer having the negative electron affinity are guided to (Continued)

an energy analyzer, and the energy of electrons excited by the solar ray is measured. Since the surface layer having the negative electron affinity is used, the photoelectrons are obtained from the electrons excited by the solar ray, and thereby energy measurement becomes possible.

20 Claims, 12 Drawing Sheets

(51) Int. Cl.
  *H01L 21/66* (2006.01)
  *H01L 31/0352* (2006.01)
  *H02S 50/15* (2014.01)
  *H01J 49/48* (2006.01)

(56) References Cited

U.S. PATENT DOCUMENTS

| | | | | |
|---|---|---|---|---|
| 6,313,461 B1 * | 11/2001 | McClelland | ............ | B82Y 15/00 250/305 |
| 6,844,688 B1 * | 1/2005 | Williams | ................ | H01S 1/02 250/492.3 |
| 7,095,037 B2 * | 8/2006 | Fernadez | ............ | B82Y 10/00 250/492.2 |
| 8,309,936 B2 * | 11/2012 | Kreckel | ............ | H01J 37/1472 250/396 R |
| 2006/0255287 A1 * | 11/2006 | Cholewa | ................ | G01T 1/28 250/397 |
| 2010/0127168 A1 * | 5/2010 | Khursheed | ............ | H01J 49/48 250/305 |

OTHER PUBLICATIONS

Mar. 11, 2014 International Search Report issued in International Patent Application No. PCT/JP2013/084497.
Mar. 11, 2014 Written Opinion issued in International Patent Application No. PCT/JP2013/084497.
Jul. 11, 2014 International Preliminary Report on Patentability issued in International Patent Application No. PCT/JP2013/084497.
Oct. 21, 2016 Search Report issued in European Patent Application No. 13868590.04.
H.-J. Drouhin et al. "Photoemission From Activated Gallium Arsenide. I. Very-High-Resolution Energy Distribution Curves". Physical Review B. Condensed Matter, vol. 31, No. 6, pp. 3859-3871, 1984.
Pierce, Daniel et al., "Photoemission of Spin-Polarized Electrons From GaAs". Physical Review B, vol. 13, No. 12, pp. 5484-5500, 1976.
Wikipedia Article: "Solar Simulator", Sep. 24, 2012.

* cited by examiner (a)

(b)

(c)

(a)

(a1)

(b)

(b1)

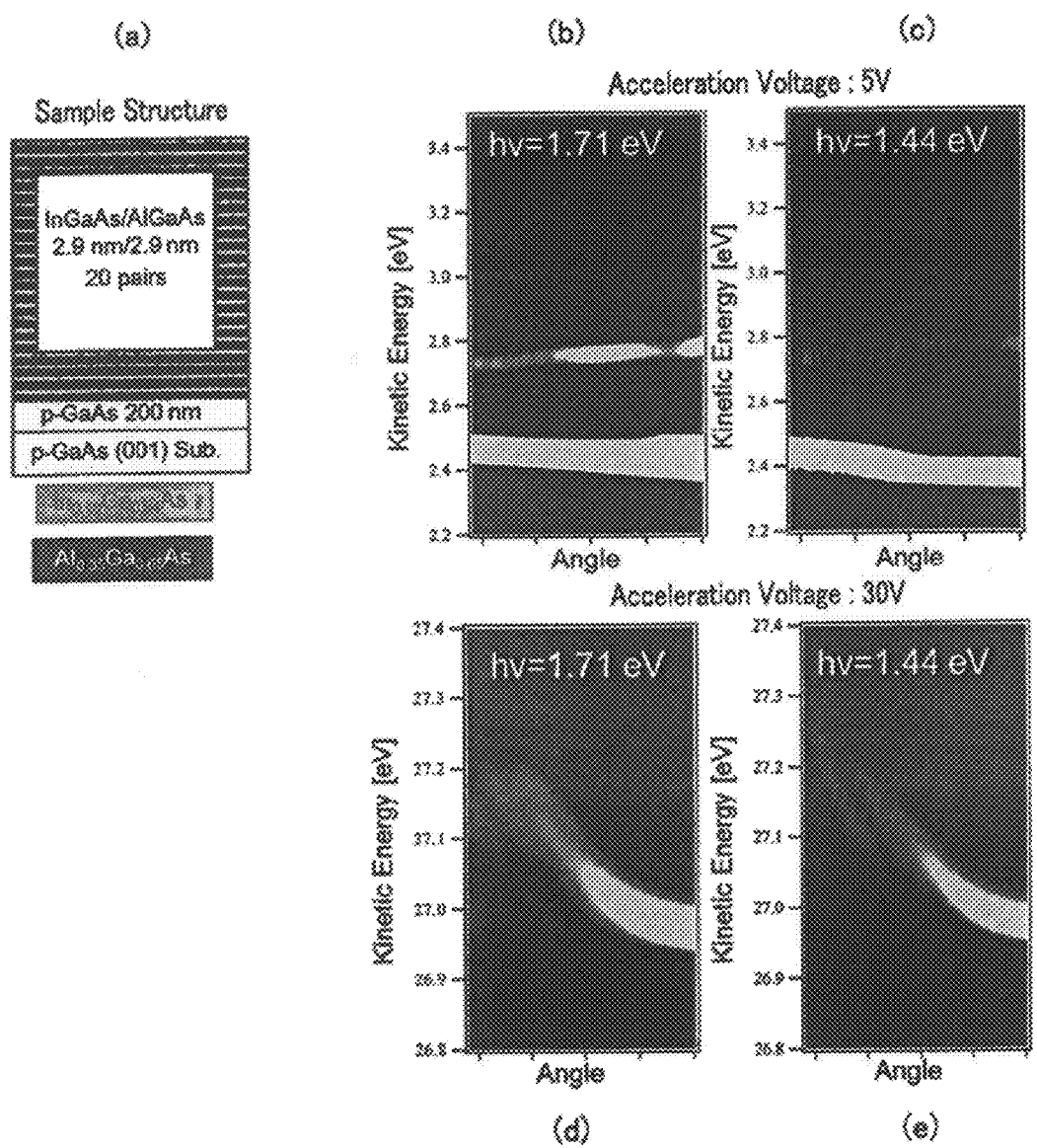

METHOD AND DEVICE FOR MEASURING ENERGY OF ELECTRONS EXCITED BY SUNLIGHT

TECHNICAL FIELD

The specification discloses a technique for measuring energy of electrons excited in a semiconductor material by exposing the semiconductor material to solar ray.

BACKGROUND ART

A solar cell provides power by use of electrons excited in a semiconductor material by exposing the semiconductor material to solar ray. The present solar cell uses electrons stable at the bottom of a conduction band due to energy relaxation of excited electrons. In, order to enhance an efficiency of the solar cell, use of hot carriers, that is, electrons before energy relaxation excited by solar ray is regarded promising. A technique of using a wide range of wavelength band included in solar ray by creating an intermediate energy level in a bandgap of a semiconductor material is also regarded promising.

In order to advance the research and development of the solar cells, it is important to measure energy of electrons excited in a semiconductor material by exposing the semiconductor material to solar ray. For example, if it is possible to know about energy of hot carriers excited or how energy of hot carriers is alleviated or relaxed, the development of solar cells using hot carriers is promoted. Alternatively, if it is possible to know about whether electrons are actually excited into an intermediate energy level or actually excited from the intermediate energy level to a conduction band, the development of solar cells using an intermediate energy level is promoted.

Unfortunately, however, a practical technique for measuring energy of electrons in a semiconductor material excited by solar ray has not been developed yet.

In order to measure energy of excited electrons present in a semiconductor material, photoelectrons emitted from the semiconductor material are needed. The energy of electrons in the semiconductor material can be measured by dispersing photoelectrons emitted from the semiconductor material.

The following techniques for photoemission spectroscopy are known.

(X-Ray Excitation Method)

As illustrated in FIG. 1, in the x-ray excitation method, an X ray is irradiated on a semiconductor material to excite electrons. The X ray has high energy and the electrons are excited to a vacuum level or more so that photoelectrons are emitted from the semiconductor material. The photoelectrons have a kinetic energy; and the kinetic energy is measured thereby to find an energy difference between a core level and the vacuum level of electrons present in the semiconductor material. When an X ray is irradiated on a semiconductor material, electrons present in the core are excited.

Since the X ray has a large half width of energy, a relationship between energy of excited electrons and energy of excitation ray cannot be known with an excellent accuracy. Of course, the method cannot be used for measuring energy of electrons excited by solar ray, which are important to the development of solar cells.

(Ultraviolet-Light Excitation Method)

As illustrated in FIG. 2, in the ultraviolet light excitation method, an ultraviolet ray is irradiated on a semiconductor material to excite electrons. An ultraviolet ray with a short wavelength has high energy, and the electrons are excited to a vacuum level or more so that photoelectrons are discharged outside the semiconductor material. The discharged photoelectrons have a kinetic energy, and the kinetic energy is measured thereby to measure energy of the electrons in occupied states of the semiconductor material.

The ultraviolet light excitation method cannot be used for measuring energy of electrons excited by solar ray, which are important to the development of solar cells.

(2-Photon Excitation Method)

As illustrated in FIG. 3, in the 2-photon excitation method, initial excitation is made by a pump light and further excitation is made by a probe light. Electrons are excited by a pump light to a conduction band, and are further excited by a probe light to a vacuum level or more. For the probe light, a harmonic wave of the pump light is used. The 2-photon excitation method needs excitation by a pulse light, and needs a complicated optical system. The 2-photon excitation method cannot be used for measuring energy of electrons excited by solar ray important to the development of solar cells.

Only energy of electrons excited to a vacuum level or more can be measured by any of the above measurement methods. Even if electrons are excited, if energy thereof is at a vacuum level or less, the energy cannot be measured. Most of the electrons excited by solar ray are at a vacuum level or less, therefore energy of the electrons excited by solar ray cannot be measured by any of the above measurement methods.

Patent Document 1 discloses therein a technique for measuring photoelectrons discharged from a substance with a low vacuum level.

With the technique in Patent Document 1, the number of photoelectrons is measured while irradiating an excitation light on hydrogen-terminated diamond. The hydrogen-terminated diamond has a negative electron affinity, and thus photoelectrons are discharged when an excitation light having low energy such as 5 eV to 5.6 eV is irradiated. Actually, the number of photoelectrons is measured while changing a wavelength of an excitation light. With the technique in Patent Document 1, it is turned out that the hydrogen-terminated diamond has a bandgap of 5.5 eV and an intermediate level due to impurities is formed at a lower level by 0.2 eV.

PRIOR ART DOCUMENTS

Patent Documents

Patent Document 1: Japanese Patent Laidopen Publication No. 2008-78369

SUMMARY OF THE INVENTION

Problems to be Solved by the Invention

The technique in Patent Document i has the following constraints.

(1) Only materials having a negative electron affinity, like hydrogen-terminated diamond, can be handled. Many semiconductor materials whose use for solar cells is being discussed do not have a negative electron affinity, and the technique in Patent Document 1 cannot be applied thereto.

(2) A relationship between the number of discharged photoelectrons and a wavelength of an excitation tight can he known, but energy of excited electrons (hot carriers) in a semiconductor material cannot be known. The technique is directed for measuring the number of photoelectrons, not for measuring energy of photoelectrons.

In the specification, there will be proposed a technique for measuring energy of electrons excited in a semiconductor material by exposing the semiconductor material to solar ray.

Solutions to the Problems

With the method disclosed in the specification, a surface layer having a negative electron affinity (NEA) is formed on a surface of a semiconductor material, the semiconductor material is placed in a vacuum environment to be exposed to solar ray, and photoelectrons discharged from the NEA surface layer are guided to an energy analyzer thereby to measure energy of the photoelectrons. With the method, energy of electrons excited by solar ray can be measured.

The semiconductor material may be exposed to actual solar ray, or may be exposed to artificial solar ray, or may be exposed to a light having a specific wavelength range included in the solar ray. In the latter case, the semiconductor material may be exposed to a spectral light of the solar ray or may be exposed to a laser light in a specific wavelength range.

With the above method, a surface layer having a negative electron affinity is formed on a surface of a semiconductor material, and thus it is not restricted by an electron affinity of the semiconductor material itself. Energy of electrons excited in a semiconductor material having a positive electron affinity can be measured.

If electrons are excited above the bottom of a conduction band, energy of hot carriers can be measured.

Further, if excited electrons are present in an intermediate energy level formed in a bandgap, energy of the electrons can be measured. Thereby, an energy level of the intermediate energy level can be known.

Consequently, behaviors of the electrons excited by irradiating solar ray on the semiconductor material can be known. It largely contributes to the research and development of solar cells.

By forming a surface layer having a negative electron affinity on a surface of a semiconductor material, it is possible to obtain photoelectrons discharged into a vacuum, but the photoelectrons discharged in vacuum need to be accelerated toward an energy analyzer in order to guide the photoelectrons into the energy analyzer. This is because a vacuum level of the space through which the photoelectrons discharged from the semiconductor material travel increases toward the energy analyzer, and hence the photoelectrons may not reach the energy analyzer unless the photoelectrons are accelerated. In a combination of the acceleration device and the energy analyzer, even if energy of the photoelectrons is low, the energy of the photoelectrons can be measured.

Energy of electrons in a semiconductor material may vary depending on a wavenumber. The wavenumber corresponds to a photoelectron emission angle. The photoelectron emission angle and the energy are measured thereby to know a band structure of the electrons in the semiconductor material. The band structure of the electrons in the semiconductor material can be known by use of the energy analyzer for resolving emission angle and energy of a photoelectron.

When photoelectrons are accelerated and guided to the energy analyzer, a travelling way of electrons can be changed by acceleration, thereby adjusting an angular resolution. With strong acceleration, photoelectrons discharged from the NEA surface layer into a wide angle range can be guided to the energy analyzer, thereby measuring a wavenumber dependence of the energy in the wide angle range. With weak acceleration, only photoelectrons discharged from the NEA surface layer into a narrow angle range can be guided to the energy analyzer, but a wavenumber dependence of the energy can be measured with high angular resolution.

A step of adjusting a voltage used to accelerate photoelectrons is preferably provided in order to adjust an angular resolution when measuring a relationship between energy and emission angle.

It may be meaningful to measure energy of electrons excited by irradiating solar ray (or pseudo solar ray), or it may be meaningful to measure energy of electrons excited by irradiating at a specific wavelength included in solar ray. The energy measurement device disclosed in the specification can achieve both of them. The wavelength bands included in solar ray may be classified into a plurality of bands. It is possible to measure energy of electrons excited per band. An influence on electrons can be measured per band of the excited light.

When solar ray is irradiated on a semiconductor material, electrons are excited not only at the irradiated surface but also in a zone distributed in the depth direction. Spectroscopic results of the energy analyzer are recorded in association with an elapse of time after the start of irradiating solar ray, thereby measuring a temporal change due to the distribution of the energy of the excited electrons in the depth direction. Findings on the distribution in the depth direction can be acquired based on the temporal change.

Reversely, also when spectroscopic results of the energy analyzer are recorded in association with an elapse of time after the end of irradiating solar ray, findings on the distribution of the energy of the excited electrons in the depth direction can be acquired.

With the measurement technique disclosed in the specification, it is possible to measure energy of electrons excited by exposing a semiconductor material to solar ray. It is possible to directly measure whether electrons are energetically relaxed after hot carriers are generated or whether hot carriers are not generated. Alternatively, it is possible to directly measure whether electrons are excited into an intermediate level formed in a bandgap or whether electrons excited to the intermediate band are further excited up to a conduction band. It largely contributes to the researches for enhancing an efficiency of solar cells.

BRIEF DESCRIPTION OF THE DRAWINGS

FIG. 13 illustrates a semiconductor material measured and measurement results according to the embodiment.

FEATURES OF THE INVENTION

Some technical features of an embodiment disclosed in the s will be described below. The following items each have technical utility.

(Feature 1) Cs and O are deposited on a surface of a semiconductor material thereby to form a NEA surface layer.

(Feature 2) Cs and O are alternately deposited on a surface of a semiconductor material thereby to form an NEA surface layer.

(Feature 3) An NEA surface layer is formed on a surface of a semiconductor material in the YO-YO method.

(Feature 4) A semiconductor material is exposed to an excitation light and the amount of discharged photoelectrons is measured while the process in the YO-YO method is advanced.

Embodiments

Figure 11:
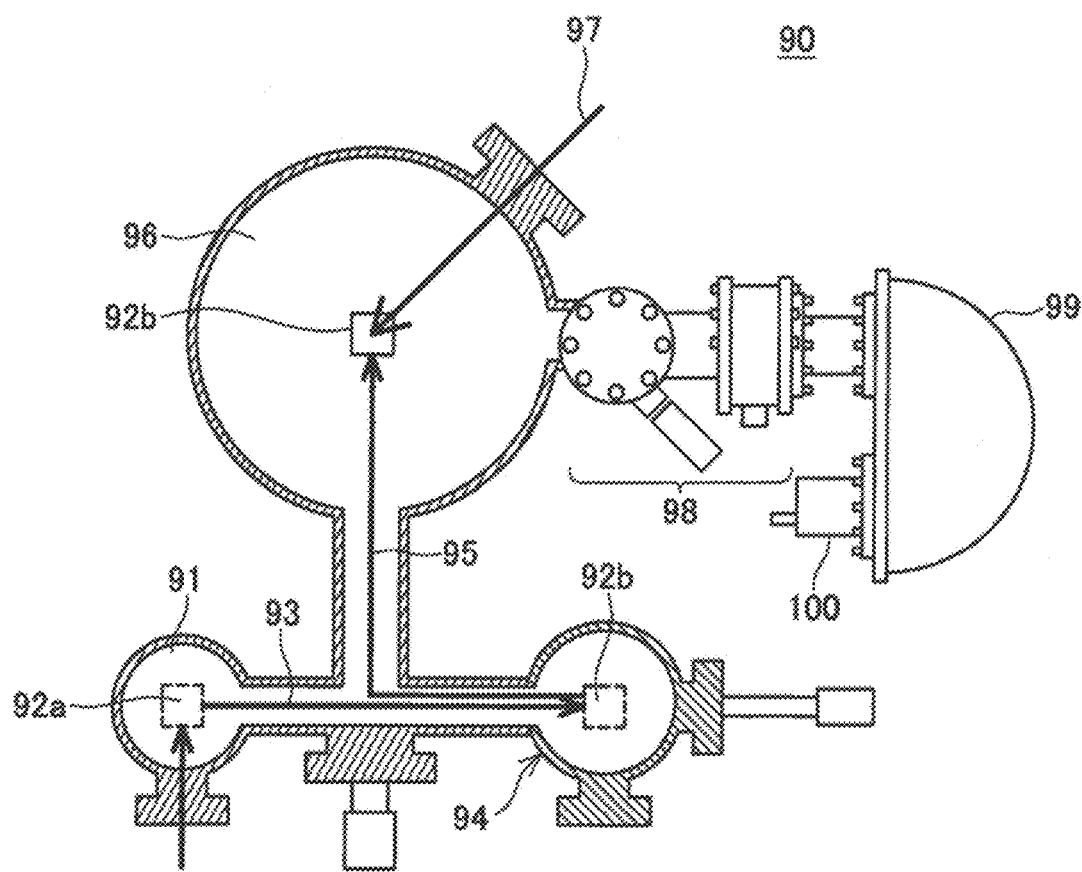
FIG. 11 illustrates an entire structure of a measurement device.

FIG. 11 illustrates an entire structure of a measurement device 90. Reference numeral 91 denotes a chamber for putting a semiconductor material as a specimen into/from the device 90. A NEA surface layer is not formed on a surface of a semiconductor material 92a to be put into the device 90. The semiconductor material 92a put into the device 90 is transferred to a NEA surface layer formation chamber 94 via a route 93. The NEA surface layer formation chamber 94 serves as a heating device and a deposition device, and is connected to vacuum pumps. When the semiconductor material 92a is sent to the NEA surface layer formation chamber 94, it is heated at 450° C. in vacuum and is held for one hour. With the heating processing, a natural oxide film formed on the surface of the semiconductor material 92a is removed. A temperature for removing the natural oxide film depends on a kind of the semiconductor material. The temperature is 450° C. for GaAs and is 1000° C. for Si. The deposition device then operates. The deposition device comprises a cesium discharge device for discharging cesium Cs and a device for introducing oxygen. The cesium discharge device is such that $CsCrO_4$ and a reducing agent are housed in a nichrome-made sleeve together with a getter agent, and is directed to discharge cesium Cs by reducing $CsCrO_4$ by supplying the heater with power for heating. The discharged cesium Cs is deposited on the surface of the semiconductor material. Oxygen is then introduced. Cesium Cs and oxygen O are alternately added on the surface of the semiconductor material so that an electric double layer potential having a thickness of several atomic layers is formed to lower a vacuum level That is, a surface layer from which electrons excited into a conduction band are discharged in vacuum is formed. Alternatively a surface layer from which electrons excited into an intermediate energy level formed in a bandgap are discharged in vacuum is formed.

The vacuum level acquired by the NEA surface layer sensitively changes according to a NEA surface layer forming condition. In order to stabilize the vacuum level acquired by the NEA surface layer, according to the present embodiment, the NEA surface layer forming process is advanced while measuring the amount of photoelectrons discharged from the surface of the semiconductor material. The energetic amount of the $CsCrO_4$ reducing heater is subjected to feedback control with the measured amount of photoelectrons as an index. With the feedback control, the vacuum level acquired by the NEA surface layer is stabilized, Reference numeral 92b denotes a semiconductor material having a NEA surface layer formed thereon. The YO-YO method is suitable for forming a NEA surface layer.

A device for introducing nitrogen fluoride such as nitrogen trifluoride $NF_3$ may be provided instead of introducing oxygen. By depositing cesium Cs and nitrogen fluoride on the semiconductor material surface, similar effects can be obtained.

The semiconductor material 92b having a NEA surface layer formed thereon is transferred to an excited electron energy measurement chamber 96 via a route 95. The chambers 91, 94, 96 and their passages are placed in a vacuum environment. Reference numeral 97 denotes a visible light laser generation device, which irradiates a visible light on the surface of the semiconductor material 92b having a NEA surface layer formed thereon. When the semiconductor material 92b is exposed to the visible light, electrons present in a valence band of the semiconductor material are excited to a conduction band. A NEA surface layer is formed on the surface of the semiconductor material 92b to lower the vacuum level so that even electrons excited by as much energy as visible light are discharged in vacuum.

Figure 1:
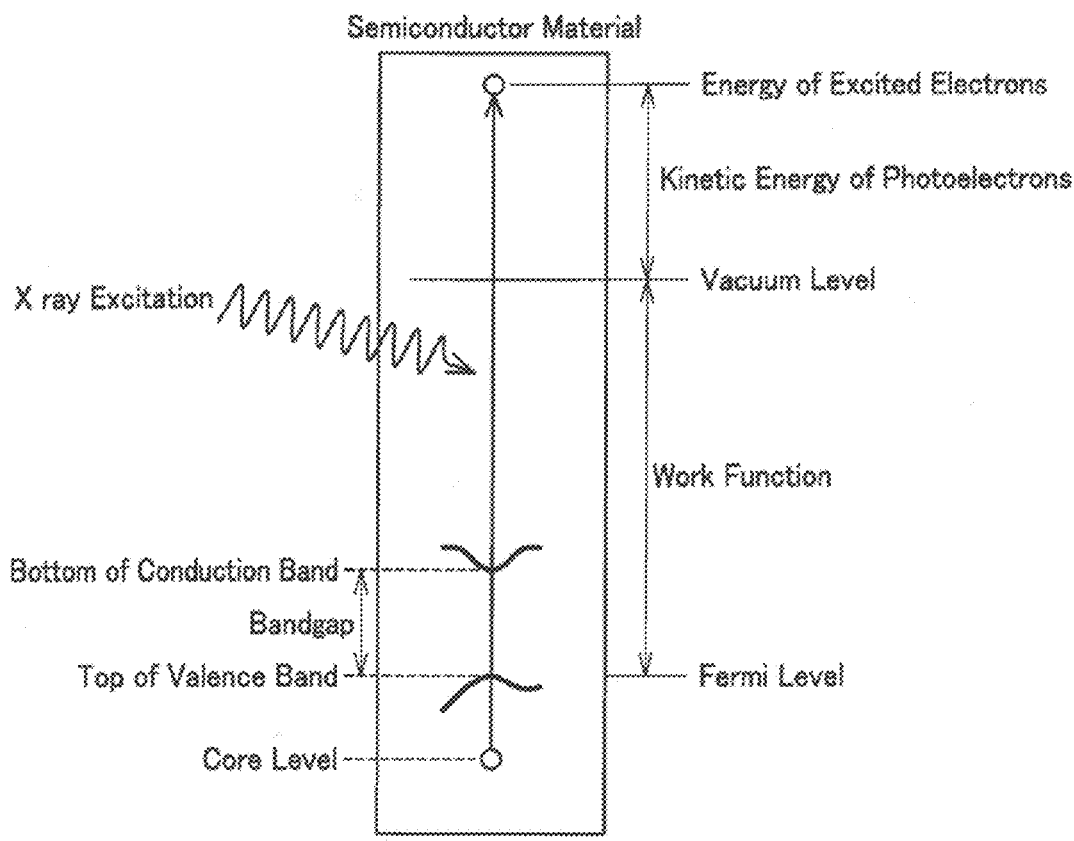
FIG. 1 illustrates a conventional method (x ray excitation method) for measuring energy of excited electrons.
Figure 2:
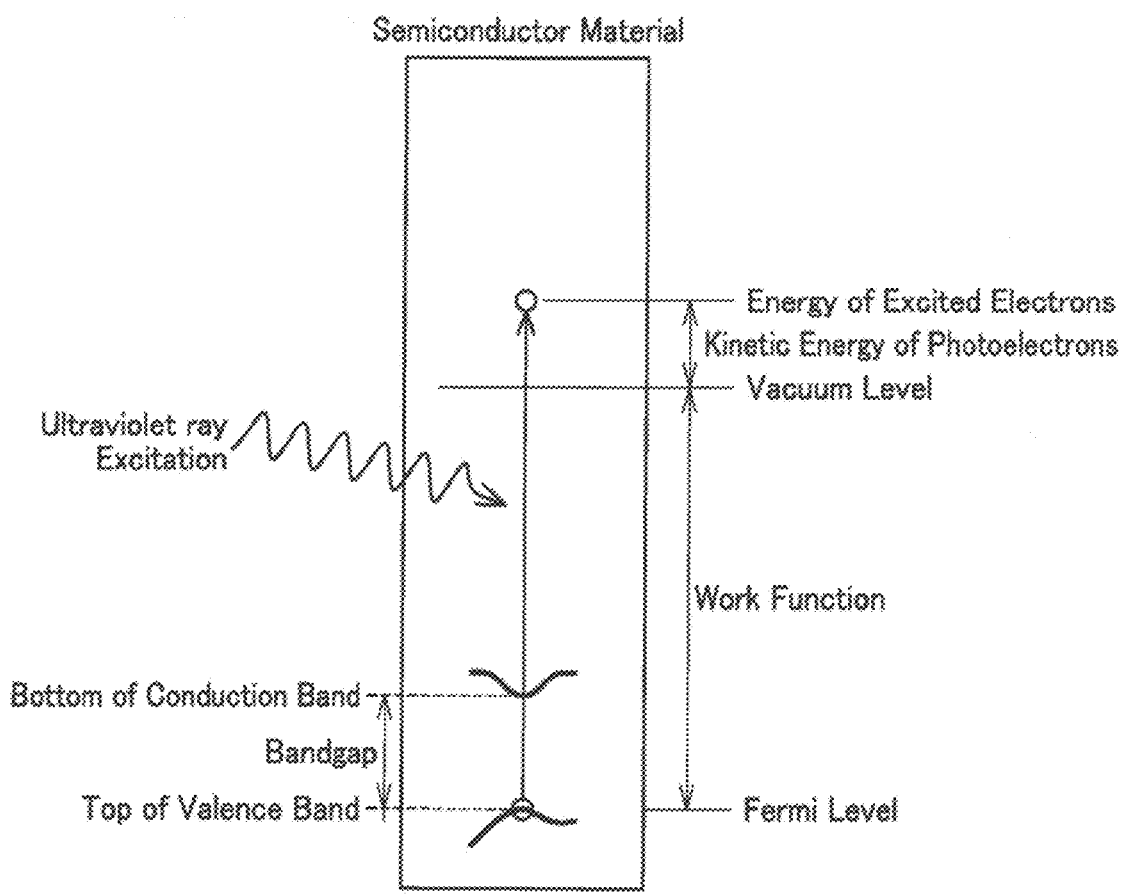
FIG. 2 illustrates a conventional method (ultraviolet light excitation method) for measuring energy of excited electrons.
Figure 3:
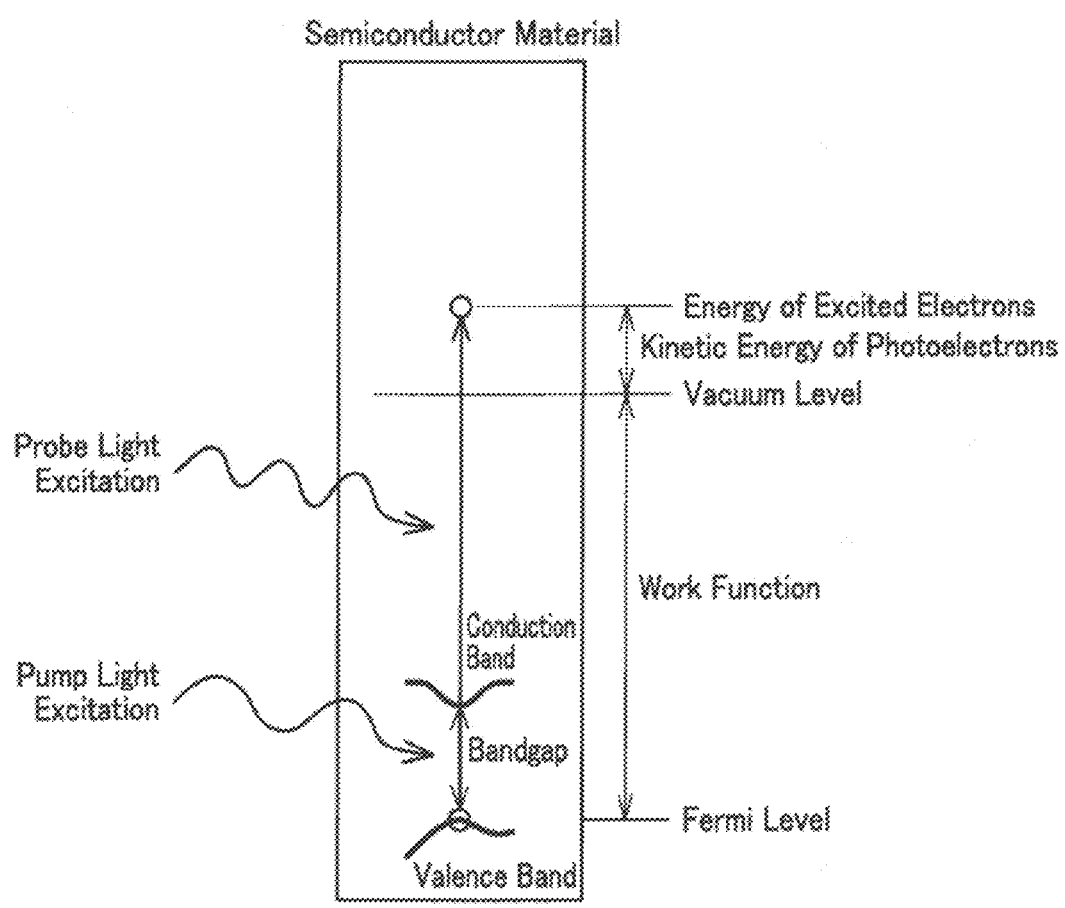
FIG. 3 illustrates a conventional method (2-photon excitation method) for measuring energy of excited electrons.
Figure 4:
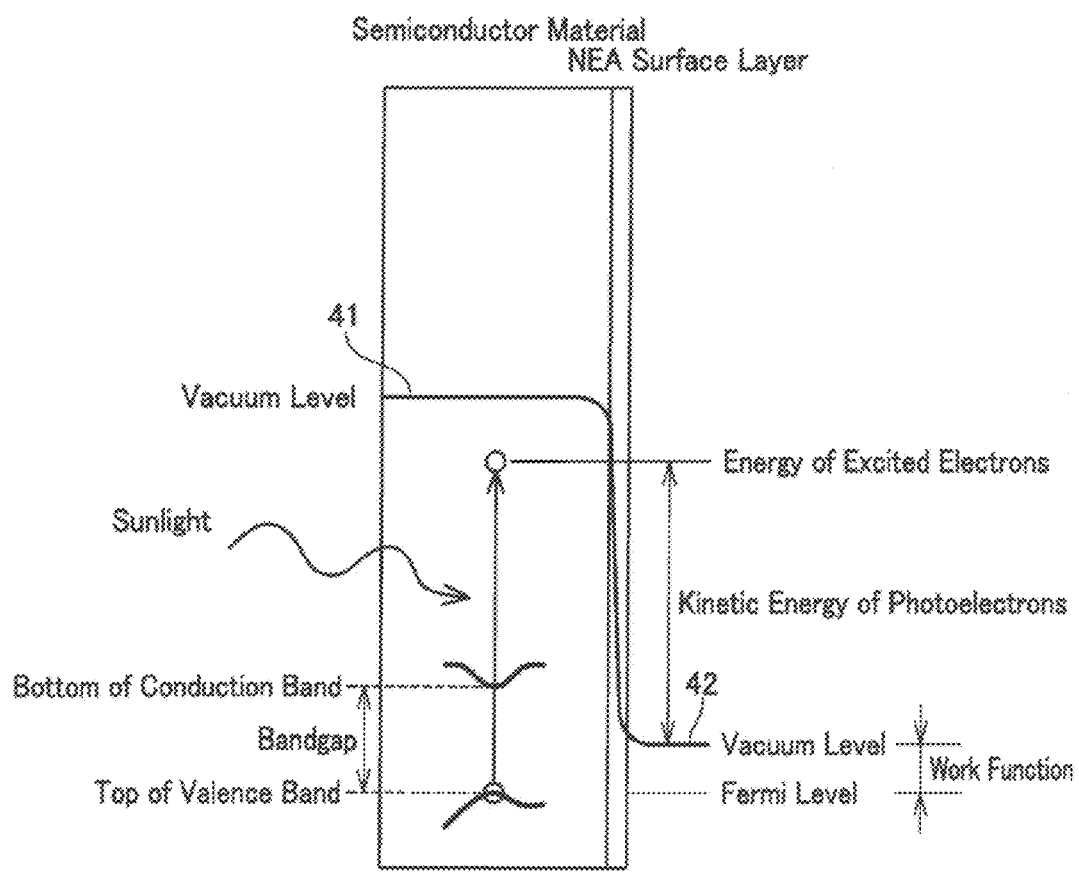
FIG. 4 illustrates a novel method for measuring energy of excited electrons.

FIG. 4 illustrates an energy level of electrons excited by a visible light. Level 41 denotes a vacuum level within a semiconductor material. The electrons excited by a visible light have lower energy than the vacuum level 41, therefore, the electrons excited by a visible light are not discharged in vacuum if a NEA surface layer is not formed. The electrons need to be excited to the level 41 or more for discharging in vacuum, and an X ray or ultraviolet ray is required for the excitation. According to the present embodiment, the vacuum level is lowered down to level 42 due to the NEA surface layer, and thus the electrons excited by a visible light are discharged in vacuum.

Figure 7:
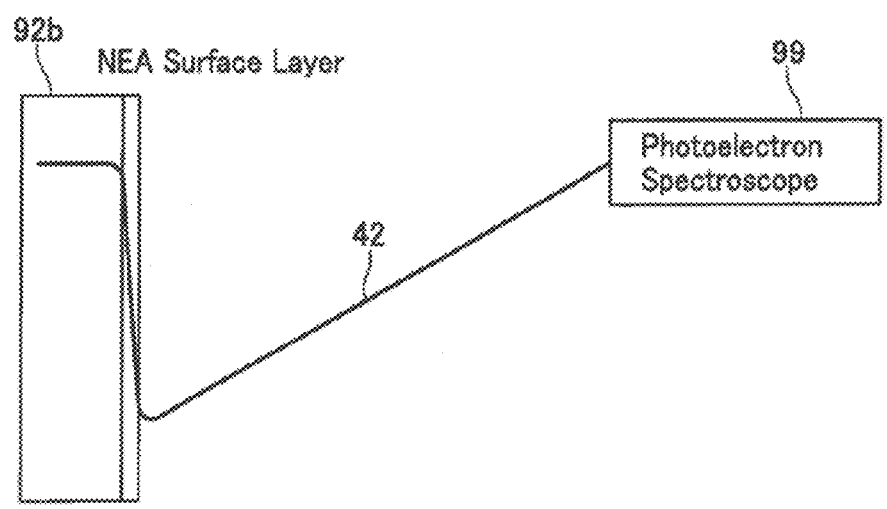
FIG. 7 illustrates a change in vacuum level between a semiconductor material and an energy analyzer.
Figure 8:
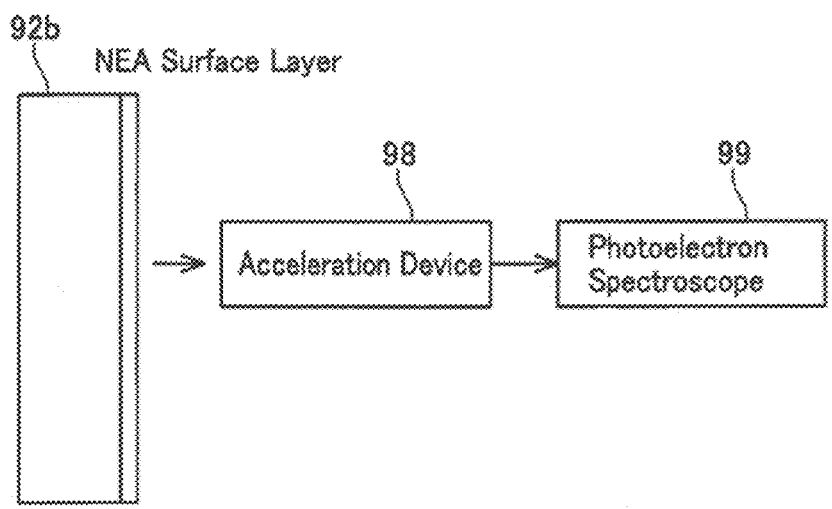
FIG. 8 illustrates an arrangement of a semiconductor material, an acceleration device and an energy analyzer.

Reference numeral 98 in FIG. 11 denotes a photoelectron acceleration device. The vacuum level at a position contacting an NEA surface layer of the semiconductor material 92b is lowered by an electric double layer provided on the NEA surface layer of the semiconductor material 92b. As illustrated in FIG. 7, however, the vacuum level 42 increases as it is further from the NEA surface layer. Therefore, photoelectrons discharged from the NEA surface layer of the semiconductor material 92b may not reach an energy analyzer (photoelectron spectroscope) 99. Alternatively, photoelectrons discharged from the NEA surface layer of the semiconductor material 92b may remain in the vicinity of the NEA surface layer, and then may cause a failure of discharge of photoelectrons. Thus, according to the present embodiment, as illustrated in FIGS. 8 and 11, an acceleration device 98 is prepared between the specimen 92b and the energy analyzer 99. The acceleration device 98 accelerates photoelectrons toward the energy analyzer 99.

The acceleration device 98 applies an electric field for acceleration so that photoelectrons acquire energy. The increased amount of energy is known, and thus energy of the excited electrons in the specimen 92b can be measured even by use of the acceleration device 98.

Figure 9:
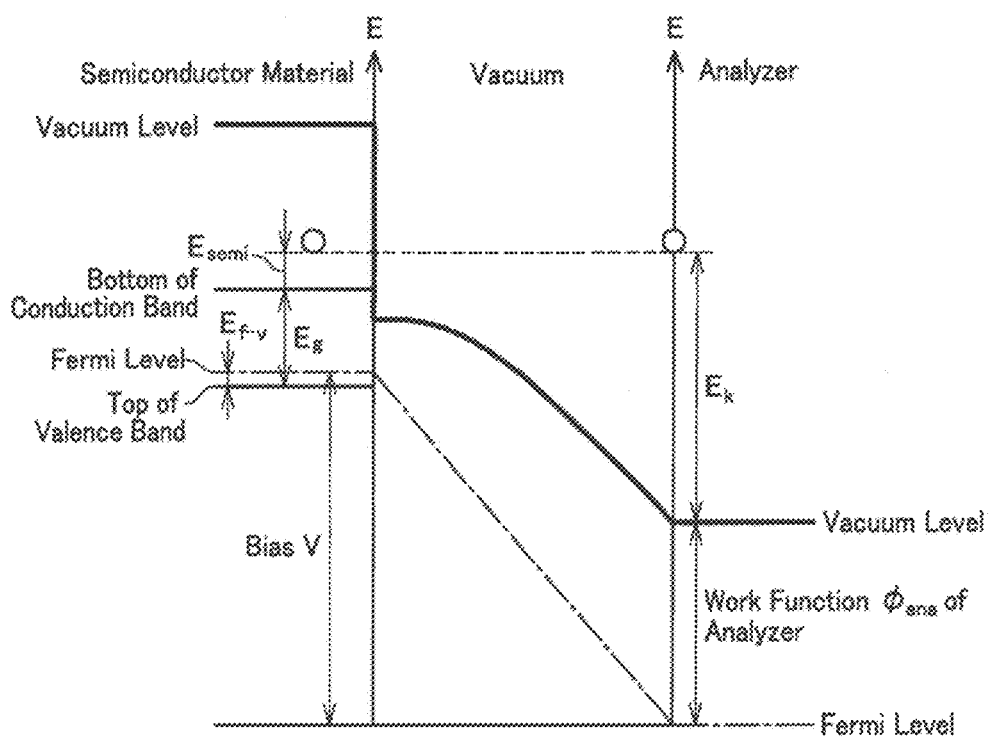
FIG. 9 illustrates a relationship between a potential in a semiconductor material and a potential of an energy analyzer.
Figure 12:
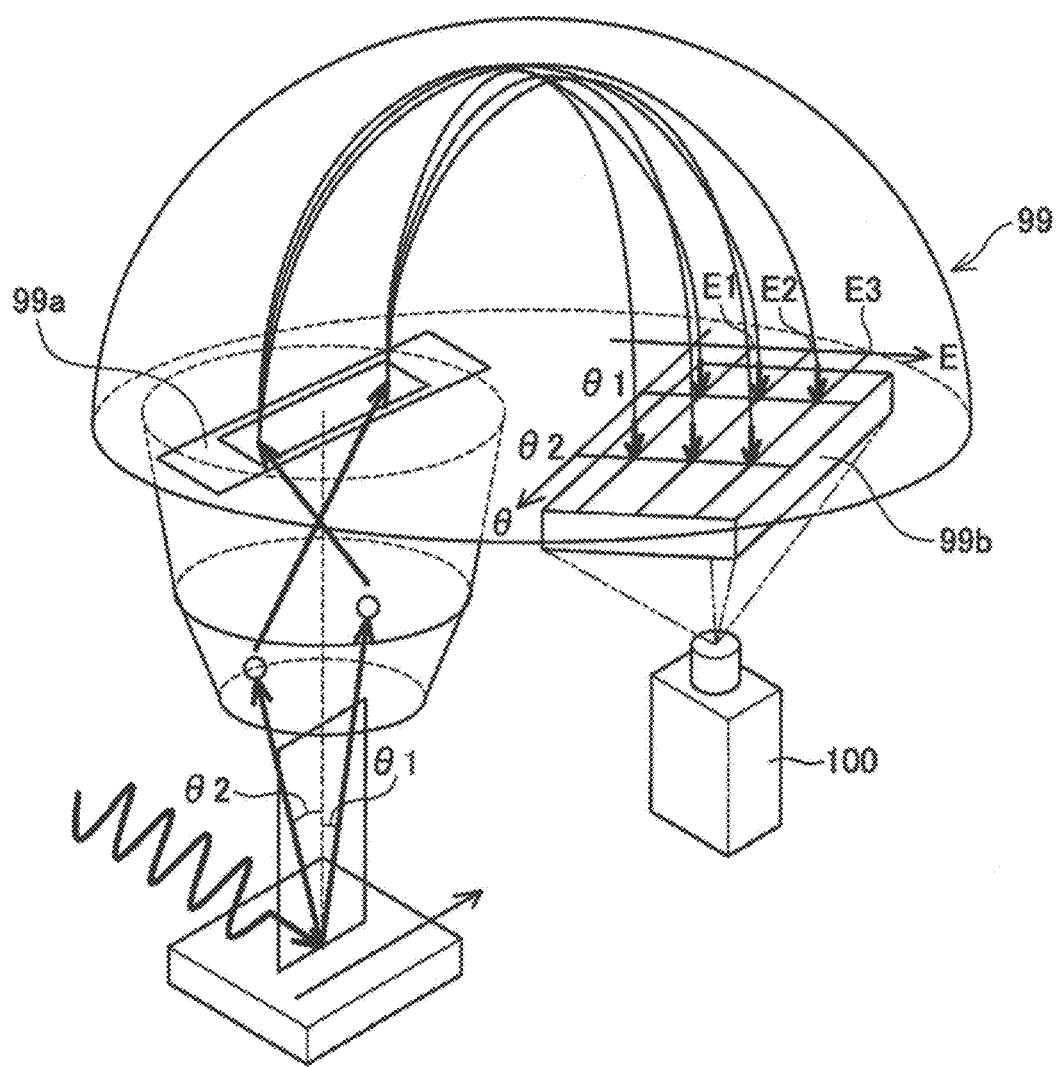
FIG. 12 illustrates an embodiment of the energy analyzer.

FIG. 9 illustrates a relationship between a potential in the semiconductor material and a potential of the energy analyzer. A Fermi level in the semiconductor material and a Fermi level of the energy analyzer are offset by a bias voltage used for acceleration. In consideration of this fact, the energy of electrons measured by the energy analyzer can be converted into energy of electrons in the semiconductor material. The conversion equation is as follows:

$$Esemi = Ek + \phi ana - V - Eg + Ef\text{-}v$$

where Esemi indicates energy of electrons excited in a semiconductor material, which is energy with reference to the bottom of the conduction band;

Ek indicates kinetic energy of photoelectrons measured by the energy analyzer, which is measured at each incident angle into the energy analyzer;

$\phi$ana indicates a work function of the energy analyzer, which can be previously measured by use of Au UPS measurement;

V indicates a bias voltage used for accelerating photoelectrons;

Eg indicates a difference between a potential at the bottom of the conduction band and a potential at the top of the valence band, which is a bandgap voltage; and Ef-v indicates a difference in potentials between a Fermi level and the top of the valence band, Reference numeral 99 in FIG. 11 denotes an energy analyzer, and reference numeral 100 denotes a CCD camera. The energy analyzer 99 and the CCD camera 100 are schematically illustrated in Fig, 12 in detail. In FIG. 12, 99b denotes a multi-channel plate, which emits a light where photoelectrons reach. The position of a light emitting point in the E axis direction is measured by the CCD camera 100 thereby to measure energy of the photoelectrons. The position of a light emitting point in the θ axis direction is measured by the CCD camera 100 thereby to measure a photoelectron discharge direction. That is, the emission angles such as θ1 and θ2 in FIG. 12 can be measured.

Figure 10:
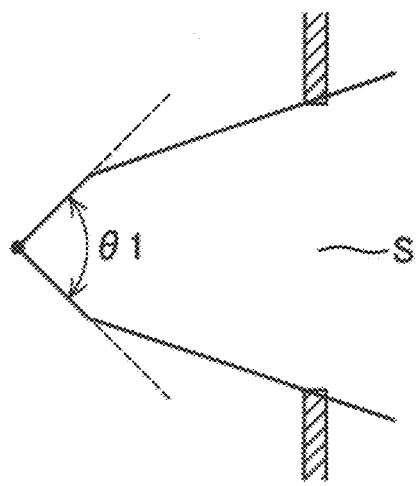
FIGS. 10(a) and 10(b) illustrate a relationship between acceleration of electrons and a measurable angle range.
Figure 10:
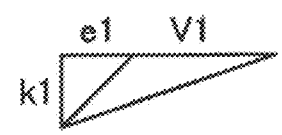
Figure 10:
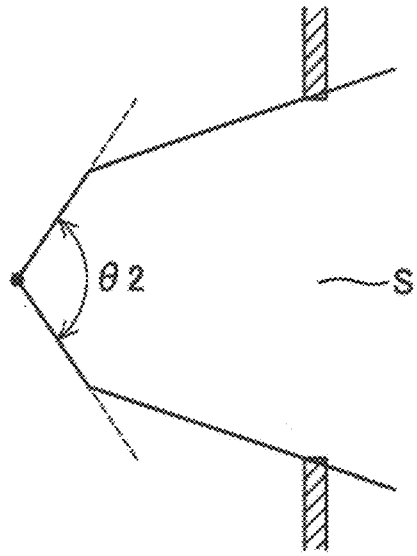
Figure 10:
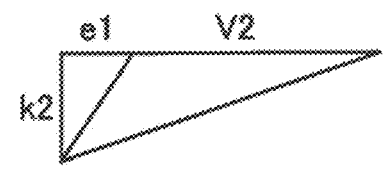

The energy analyzer 99 measures energy and incident angle of electrons incident into a slit 99a. FIG. 10(a) illustrates a range θ1 of a discharge angle incident into a slit S when photoelectrons are weakly accelerated. FIG. 10(b) illustrates a range θ2 of a discharge angle incident into the slit S when photoelectrons are strongly accelerated. V1 at (a1) in FIG. 10 indicates a bias voltage for weak acceleration, and V2 at (b1) indicates a bias voltage for strong acceleration, V1<V2 is assumed. Reference numeral e1 indicates kinetic energy in a direction in which non-accelerated photoelectrons travel in the energy analyzer, which is equal at both (a1) and (b1) in FIG. 10. Reference numerals k1 and k2 are wavenumbers, and as they are higher, the kinetic energy in a direction along the surface is larger. If k1<k2 is assumed, as is clear based on a comparison between (a1) and (b1) in FIG. 10, the directions in which photoelectrons after acceleration travel match with each other at V1<V2. In this case, θ1 is smaller than θ2. Measurement can be made in a wide emission angle θ2 by measurement with strong acceleration (contrary, an angular resolution is lower) Measurement can be made only in a narrower emission angle θ1 by measurement with weak acceleration, but an angular resolution is higher. With the device in FIG. 11, a voltage to be applied to the acceleration device 98 can be adjusted in order to adjust an angular resolution or to adjust emission angle range measured at a time.

When a bias voltage V is changed, a focus position of an electron beam incident into the energy analyzer 99 is offset, which influences a spectroscopic result. With the device in FIG. 11, a compensation circuit for adjusting a focus position of a condensing lens in association with a voltage applied to the acceleration device is added, and even if a bias voltage to be applied to the acceleration device 98 is changed, the focus position of an electron beam incident into the energy analyzer 99 does not change.

Figure 6:
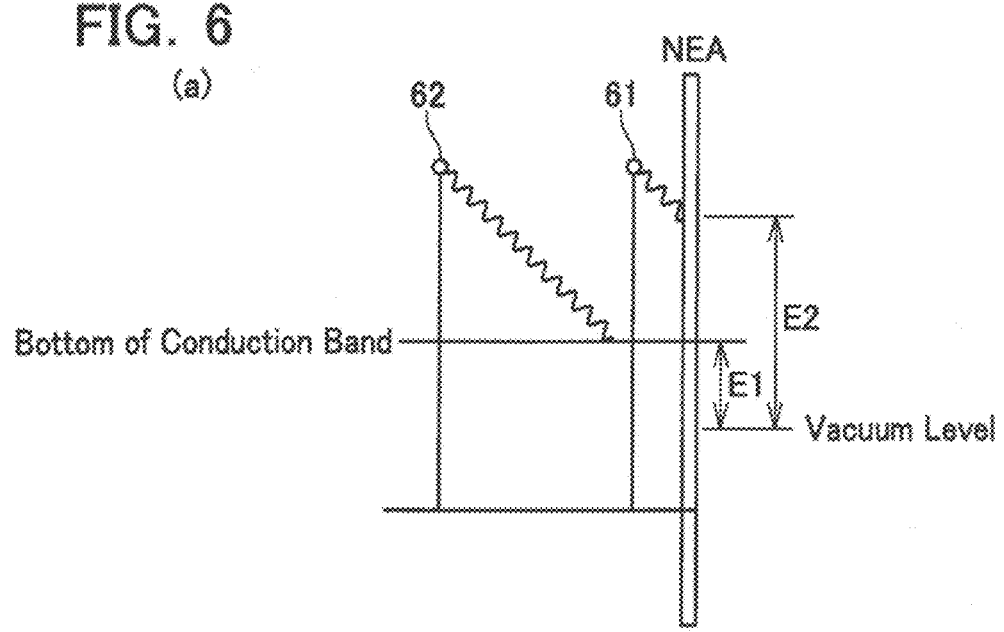
FIGS. 6(a) to 6(c) illustrate findings obtained by measuring energy of excited electrons in time sequence.
Figure 6:
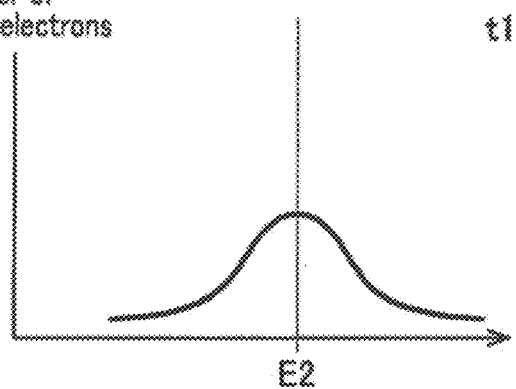
Figure 6:
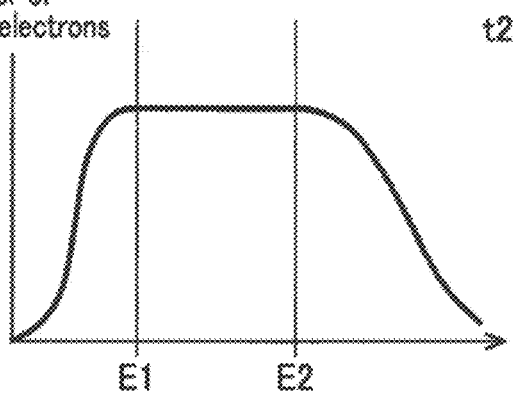

FIG. 6(b) illustrates a spectroscopic result measured at ti time after a start of a visible light irradiation on the specimen 92b. The horizontal axis indicates a kinetic energy of photoelectrons and the vertical axis indicates the number of photoelectrons. FIG. 6(c) indicates a spectroscopic result measured at t2 time after the start of the visible light irradiation on the specimen 92b. t1<t2 is assumed. The kinetic energy of photoelectrons takes a maximum frequency of E2 at t1. The kinetic energy of photoelectrons widely distributes between E1 and E2 at t2.

In FIG. 6(a), reference numeral 61 denotes an electron excited at a position close to the NEA surface layer. The excited electrons move in the semiconductor material and are discharged in vacuum when reaching the NEA surface layer. While the excited electrons move in the semiconductor material, energy of the excited electrons is alleviated. The electrons excited at a position extremely close to the NBA surface layer are discharged as photoelectrons before little energy thereof is alleviated. The photoelectrons measured immediately after the start of irradiating a visible light depend on the electrons excited, at a position extremely close to the NEA surface layer, and can be regarded as having energy equal to energy before energy relaxation.

In FIG. 6(a), reference numeral 62 denotes an electron excited at a position away from the NEA surface layer. Electrons excited away from the NEA surface layer are discharged as photoelectrons after energy thereof is alleviated. The photoelectrons measured after the start of irradiating a visible light include photoelectrons derived from the electrons excited away from the NEA surface layer and photoelectrons derived from the electrons excited at a position extremely close to the NEA surface layer, and have various types of energy from the energy (E1) after relaxation to the energy (E2) before energy relaxation.

When a spectroscopic result of photoelectrons is analyzed in association with an elapsed time after the start of irradiating a visible light, a distance from the NEA surface layer and a progress of energy relaxation can be understood in an associated manner, thereby measuring an energy relaxation distance or the like.

Similarly, also when a spectroscopic result of photoelectrons is analyzed in association with an elapse of time after the end of irradiating a visible light, a distance from the NEA surface and a progress of energy relaxation can be understood in an associated manner, thereby measuring an energy relaxation distance or the like.

FIG. 13(a) illustrates a semiconductor material used for measurement. A semiconductor material with a superlattice structure is measured. A superlattice specimen is made by the organic metal vapor deposition method. As illustrated in FIG. 13(a), a 200-nm p-GaAs buffer layer is grown on a p-GaAs(001) substrate, and 20 pairs of 2.9-nm $Al_{0.35}Ga_{0.65}As$ barrier layer and 2.9-nm $In_{0.16}Ga_{0.84}As$ well layer are alternately grown thereon. Zn doping concentration of the superlattice layer is $5 \times 10^{18}$ cm$^{-3}$.

After the specimen is heated at 450° C. In the NEA surface layer formation chamber 94, and heated and cleaned for one hour, a NEA surface layer is prepared by use of the Yo-Yo method.

Then, the specimen is transferred to the measurement chamber 96 to make angular-resolved VPS (Visible light Photoelectron Spectroscopy) measurement. The measurement is made by applying a bias of −5 V or −30 V (accelerating voltage) on the specimen. The excited light employs a visible light having energy of 1.71 eV or 1.44 eV.

FIGS. 13(b) to 13(e) illustrate photoelectron distribution mapping images measured by the energy analyzer 99, respectively.

FIGS. 13(b) and 13(d) illustrate the measurement results with excitation light energy of 1.71 eV, FIGS. 13(c) and 13(e) illustrate the measurement results with excited light energy of 1.44 eV, FIGS. 13(b) and 13(c) illustrate the measurement results with a bias voltage for acceleration of 5 V, and FIGS. 13(d) and 13(e) illustrate the measurement results with a bias voltage for acceleration of 30 V, where the vertical axis indicates energy and the horizontal axis indicates an detected angle of photoelectrons. Photoelectrons with higher energy are observed at excited light energy of 1.71 eV than at 1.44 eV. It is confirmed that energy of hot carriers can be measured. Further, as the bias voltage is larger, photoelectrons discharged into a wider angle range are observed. An angle at which electrons are measured corresponds to a wavenumber of band dispersion of a semiconductor, and thus an image with a larger curvature can be obtained in a mapping image.

A pseudo solar ray source may be employed instead of the visible light laser generation device 97 in FIG. 11. By use of the pseudo solar ray source, energy of excited electrons when the specimen 92b is exposed to solar ray can be measured. The visible light laser generation device 97 may generate a visible light in a specific wavelength band in visible lights. By use of a visible light laser generation device capable of changing a wavelength, energy of excited electrons when the specimen 92b is exposed to, for example, a red light can be measured or energy of excited electrons when the specimen 92b is exposed to, for example, a blue light can be measured.

Figure 5:
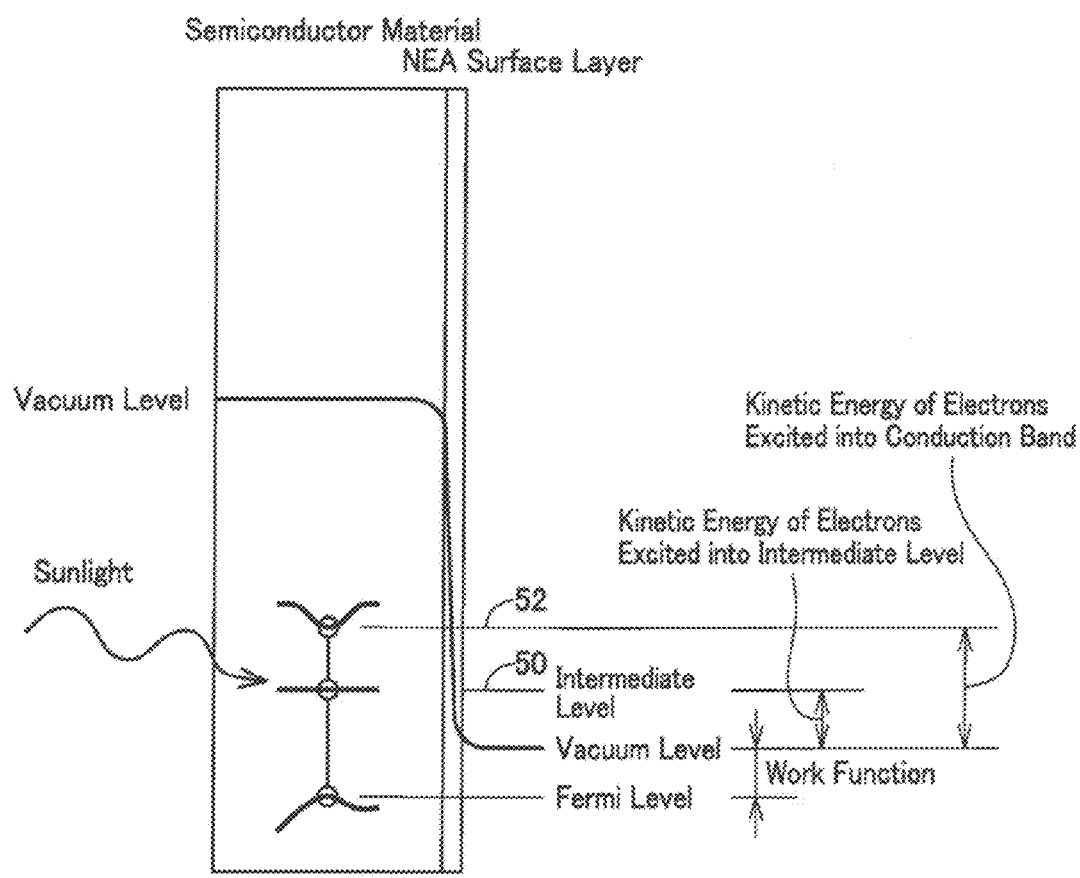
FIG. 5 illustrates a novel method for measuring energy of electrons excited in an intermediate energy level.

FIG. 5 illustrates a solar cell in which an intermediate energy level is formed within a bandgap by use of a quantum structure in order to widen a wavelength range used for solar cell. In this case, it is expected that electrons are excited into the intermediate level by a red light or an infrared light included in solar ray and are farther excited in the conduction band.

According to the present embodiment, the vacuum level can be lowered to the intermediate energy level or less. Therefore, if excited electrons are present: in the intermediate energy level, energy of the electrons can be measured. The effects generated by the intermediate energy level can be examined.

For the device according to the present embodiment, a resolution of the energy analyzer is 5 meV or less, and an energy width of a laser light of the light source is 0.1 meV or less. Consequently, a resolution of the measurement device is around 5 meV. An energy width of the intermediate energy level is 100 meV in many cases. With the measurement device and the measurement method according to the present embodiment, a distribution of electrons excited into the intermediate energy level can be measured.

According to the present embodiment, a group of photoelectrons is resolved by energy, and an energy distribution of the group of photoelectrons is measured based on the positions in the E axis direction of FIG. 12 and the number of photoelectrons. In place of this, a technique for measuring the number of photoelectrons with energy of a threshold or more may be employed. For example, when the number of photoelectrons with energy of E1 or more is p1 and the number of photoelectrons with energy of $E1+\Delta E$ or more is $p1-\Delta p$, it can be seen that $\Delta p$ photoelectrons with energy of E1 to $E1+\Delta E$ are present.

Similarly, in the above embodiment, a group of photoelectrons is dispersed by a wavenumber (emission angle of photoelectrons) and a wavenumber distribution of the group of photoelectrons is measured based on the positions in the θ axis direction of FIG. 12 and the number of photoelectrons. In place of this, a technique for measuring the number of photoelectrons having emission angle of a threshold or less may be employed. For example, when the number of photoelectrons with emission angle of θ1 or less is q1 and the number of photoelectrons with emission angle of $\theta1+\Delta\theta$ or less is $q1+\Delta q$, it can be seen that $\Delta q$ photoelectrons with emission angle of θ1 to $\theta1+\Delta\theta$ are present.

A relationship between emission angle θ and wavenumber k can be theoretically calculated. However, the positions in the θ axis direction of FIG. 12 may be offset from emission angle of photoelectrons in the actual measurement device.

In the actual measurement device, the specimen 92b illustrated in FIG. 8 is supported by a sample holder. The sample holder is placed on the left of the specimen 92b. Generally, the sample holder is larger than the specimen 92b, and when the specimen 92b is observed from the right side of FIG. 8, the sample holder is observed around the specimen 92b. The vacuum levels of the specimen 92b and the sample holder are different from each other. Therefore, a direction in which photoelectrons discharged from the specimen travel can he changed. For example, photoelectrons discharged from the specimen 92b may be absorbed toward the sample holder present around the specimen 92b. A relationship between a position in the θ axis direction of FIG. 12 and a wavenumber may be different from a theoretical value due to the sample holder. In order to avoid the error, a small-sized sample holder, which is hidden behind the specimen 92b, is advantageously employed. It is advantageous that no impact is given to the direction in which photoelectrons discharged in a direction normal to the surface of the specimen 92b travel. Thus, it is advantageous that a planar shape of the specimen 92b is circular, a planar shape of the sample holder is also circular, and both of them are coaxial.

Alternatively, a technique for compensating for an impact of the sample holder is useful. A mesh is placed on the photoelectron discharge surface of the specimen 92b and a voltage is applied to the mesh, thereby compensating for an impact of the sample holder.

Specific examples of the present invention have been described above in detail, but are merely exemplary and do not intend to limit the scope of claims. The techniques in claims include various variants and modifications of the specific examples described above.

The technical components described in the specification and the drawings demonstrate technical utility solely or in various combinations, and are not limited to the combinations described in claims on application. The technique described in the specification or drawings by way of example attains a plurality of objects at the same time, and has technical utility by attaining one of the objects.

DESCRIPTION OF REFERENCE SIGNS

90: Measurement device
91: Chamber for putting semiconductor material into/from device
92a: Semiconductor material before NEA surface layer is formed
92b: Semiconductor material after NEA surface layer is formed
94: NEA surface layer formation chamber 96: Excited electron energy measurement chamber
97: Visible light laser generation device
98: Acceleration device
99: Energy analyzer
100: CCD camera

The invention claimed is:

1. A method for measuring energy and wavenumber of electrons within a semiconductor material excited by solar ray, the method comprising:
forming a surface layer having a negative electron affinity on a surface of the semiconductor material;
exposing the semiconductor material to the solar ray in a vacuum environment;
accelerating photoelectrons discharged from the surface layer toward an energy analyzer; and
dispersing the photoelectrons incident into the energy analyzer based on energy and emission angle of the photoelectrons.

2. The method according to claim 1, further comprising:
adjusting a voltage used for acceleration to adjust an angular resolution.

3. The method according to claim 1, wherein
the semiconductor material is exposed at a specific wavelength in the solar ray.

4. A method for measuring temporal change of energy of electrons within a semiconductor material excited by solar ray, the method comprising:
forming a surface layer having a negative electron affinity on a surface of the semiconductor material;
exposing the semiconductor material to the solar ray in a vacuum environment;
accelerating photoelectrons discharged from the surface layer toward an energy analyzer;
dispersing the photoelectrons incident into the energy analyzer based on energy of the photoelectrons repeatedly, and
recording the spectroscopic result with an elapse of time after the start of exposing to the solar ray.

5. The method according to claim 4, further comprising:
adjusting a voltage used for acceleration to adjust an angular resolution.

6. The method according to claim 4, wherein
the semiconductor material is exposed at a specific wavelength in the solar ray.

7. A method for measuring temporal change of energy of electrons within a semiconductor material excited by solar ray, the method comprising:
forming a surface layer having a negative electron affinity on a surface of the semiconductor material;
exposing the semiconductor material to the solar ray in a vacuum environment;
accelerating photoelectrons discharged from the surface layer toward an energy analyzer;
dispersing the photoelectrons incident into the energy analyzer based on energy of the photoelectrons repeatedly, and
recording the spectroscopic result with an elapse of time after the end of exposing to the solar ray.

8. The method according to claim 7, further comprising:
adjusting a voltage used for acceleration to adjust an angular resolution.

9. The method according to claim 7, wherein
the semiconductor material is exposed at a specific wavelength in the solar ray.

10. A device for measuring energy of electrons within a semiconductor material excited by solar ray, the device comprising:
a chamber for forming a surface layer having a negative electron affinity;
a chamber for exposing the semiconductor material to the solar ray;
an acceleration device for accelerating photoelectrons discharged from the surface layer of the semiconductor material;
an energy analyzer for dispersing the photoelectrons accelerated by the acceleration device; and
a recording device of recording spectroscopic result with an elapse of time;
wherein the energy analyzer disperses based on energy of the photoelectrons discharged from the semiconductor material.

11. The device according to claim 10, further comprising:
a voltage adjustment device for adjusting a voltage to be applied to the acceleration device.

12. A method for measuring energy and wavenumber of electrons within a semiconductor material excited by visible light, the method comprising:
forming a surface layer having a negative electron affinity on a surface of the semiconductor material;
exposing the semiconductor material to the visible light in a vacuum environment;
accelerating photoelectrons discharged from the surface layer toward an energy analyzer; and
dispersing the photoelectrons incident into the energy analyzer based on energy and emission angle of the photoelectrons.

13. A method for measuring temporal change of energy of electrons within a semiconductor material excited by visible light, the method comprising:
forming a surface layer having a negative electron affinity on a surface of the semiconductor material;
exposing the semiconductor material to the visible light in a vacuum environment;
accelerating photoelectrons discharged from the surface layer toward an energy analyzer;
dispersing the photoelectrons incident into the energy analyzer based on energy of the photoelectrons repeatedly, and
recording the spectroscopic result with an elapse of time after the start of exposing the semiconductor material to the visible light.

14. A method for measuring temporal change of energy of electrons within a semiconductor material excited by visible light, the method comprising:
forming a surface layer having a negative electron affinity on a surface of the semiconductor material;
exposing the semiconductor material to the visible light in a vacuum environment;
accelerating photoelectrons discharged from the surface layer toward an energy analyzer;
dispersing the photoelectrons incident into the energy analyzer based on energy of the photoelectrons repeatedly, and
recording the spectroscopic result with an elapse of time after the end of exposing the semiconductor material to the visible light.

15. A device for measuring energy and wavenumber of electrons within a semiconductor material excited by visible light, the device comprising:
a chamber capable of forming a surface layer having a negative electron affinity;
a chamber for exposing the semiconductor material to the visible light;

an acceleration device for accelerating photoelectrons discharged from the surface layer of the semiconductor material;

an energy analyzer for dispersing the photoelectrons accelerated by the acceleration device based on energy and emission angle of the photoelectrons discharged from the semiconductor material.

16. The device according to claim 15, further comprising:

a recording device of recording spectroscopic result with an elapse of time.

17. The device according to one of claim 15, further comprising:

a voltage adjustment device for adjusting a voltage to be applied to the acceleration device.

18. A device for measuring energy and wavenumber of electrons within a semiconductor material excited by visible light, the device comprising:

a chamber capable of heating the semiconductor material, depositing on the semiconductor material and irradiating the visible light to the semiconductor material;

an acceleration device for accelerating photoelectrons discharged from a surface of the semiconductor material;

an energy analyzer for dispersing the photoelectrons accelerated by the acceleration device based on energy and emission angle of the photoelectrons discharged from the semiconductor material.

19. The device according to claim 18, further comprising:

a recording device of recording spectroscopic result with an elapse of time.

20. The device according to one of claim 18, further comprising:

a voltage adjustment device for adjusting a voltage to be applied to the acceleration device.

\* \* \* \* \*